United States Patent [19]

Ladewig et al.

[11] 4,354,046
[45] Oct. 12, 1982

[54] PROCESS FOR OBTAINING HIGH PURITY BISPHENOL A

[75] Inventors: Glen R. Ladewig; Feng-Chih Chang, both of Angleton, Tex.

[73] Assignee: The Dow Chemical Company, Midland, Mich.

[21] Appl. No.: 267,191

[22] Filed: May 26, 1981

[51] Int. Cl.³ .............................................. C07C 37/84
[52] U.S. Cl. .................................. 568/724; 568/749; 568/753
[58] Field of Search ............... 568/724, 727, 749, 753

[56] References Cited

U.S. PATENT DOCUMENTS

| | | | |
|---|---|---|---|
| 2,182,308 | 12/1939 | Britton et al. | 260/619 |
| 2,191,831 | 2/1940 | Perkins | 260/619 |
| 2,791,616 | 5/1957 | Luten, Jr. | 260/619 |
| 3,049,568 | 8/1962 | Apel et al. | 260/619 |
| 3,049,569 | 8/1962 | Apel et al. | 260/619 |
| 3,073,868 | 1/1963 | Prahl et al. | 260/619 |
| 3,207,795 | 9/1965 | Prahl et al. | 260/619 |
| 3,219,549 | 11/1965 | Prahl et al. | 202/52 |
| 3,221,061 | 11/1965 | Grover et al. | 260/619 |
| 3,290,390 | 12/1966 | Prahl et al. | 260/619 |
| 3,326,986 | 6/1967 | Dugan et al. | 260/619 |
| 3,394,089 | 7/1968 | McNutt et al. | 260/2.2 |
| 3,418,378 | 12/1968 | MacNaughton et al. | 260/619 |
| 3,535,389 | 10/1970 | de Jong | 260/619 |
| 3,673,262 | 6/1972 | Prahl et al. | 260/619 |
| 3,919,330 | 11/1975 | Kwantes et al. | 568/724 |
| 4,079,087 | 3/1978 | Sun | 260/619 |
| 4,107,218 | 8/1978 | Konrad et al. | 560/724 |
| 4,156,098 | 5/1979 | Li | 568/724 |
| 4,242,527 | 12/1980 | Marks et al. | 568/724 |

Primary Examiner—Werren B. Lone
Attorney, Agent, or Firm—A. C. Ancona

[57] ABSTRACT

A method of purifying bisphenols by (1) crystallizing the crude bis from a single liquid phase containing water, bis and an organic solvent, (2) stripping the remaining mother liquor (containing the impurities) of solvent and water, and (3) mixing it with phenol, (4) contacting the mixture of phenol and mother liquor with a cation exchange resin to convert the impurity to the desired product, (5) stripping the phenol and (6) recycling the remainder to the initial crystallizing step.

5 Claims, 1 Drawing Figure

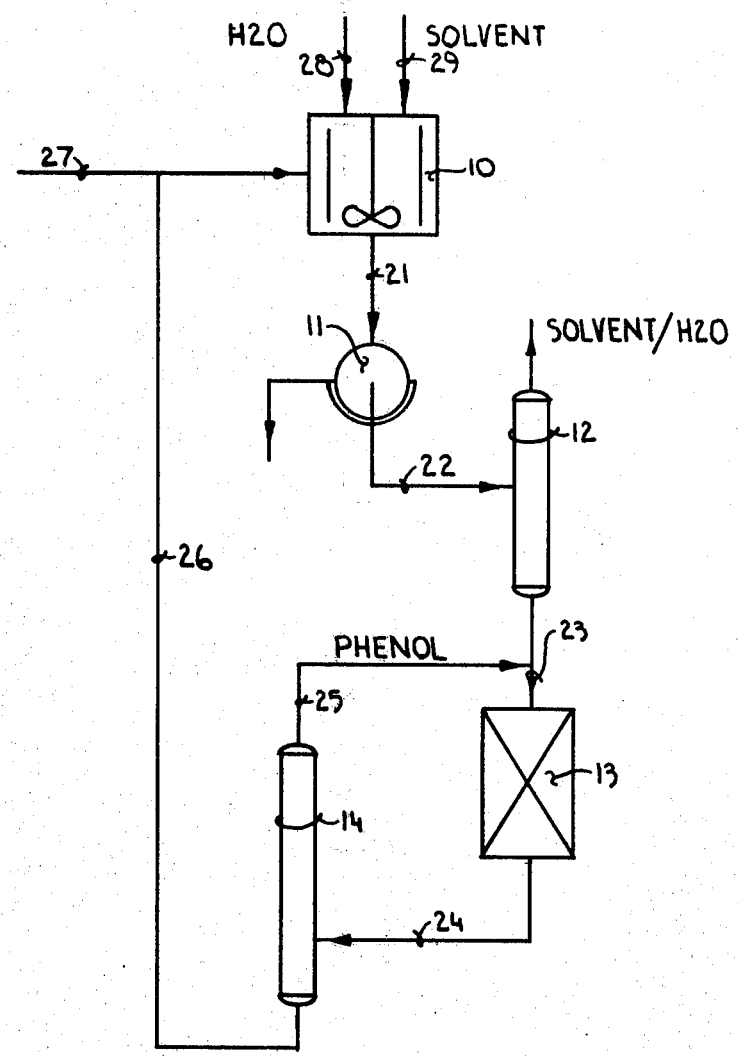

PROCESS FOR OBTAINING HIGH PURITY BISPHENOL A

BACKGROUND OF THE INVENTION

Bisphenol A, 2,2'-bis(4-hydroxyphenyl)propane*, is widely used in the manufacture of epoxy resins and polycarbonates. Bisphenol A is usually prepared by the condensation of phenol and acetone in the presence of an acid catalyst with a sulfur-containing promoter. However, the reaction between phenol and acetone to form 2,2'-bis(4-hydroxyphenyl)propane using any known catalyst always produces a number of by-products. It is well known that the purity of bisphenol A is very important with regard to the quality of polymers which are prepared therefrom. In the production of polycarbonates, bisphenol A purity requirement is much higher than that of the product obtained by any production method without further purification. Typical commercial bisphenol was found to contain 4% o,p'-isomer, 3% trisphenol I and 1% Dianins compound (Anal. Chem. 31, 1214–17, 1959). There are many patents related to the purification of bisphenol; and the extent of the purification necessary is dependent on yield, crude bisphenol purity, and quality of final product desired. One method suggested is the formation of a 1:1 crystalline complex with phenol (U.S. Pat. No. 2,791,616). The phenol complex may be refined by washing with phenol, after which it is remelted and heated under vacuum to decompose the complex and distill out the phenol.

*Also called 4,4'-isopropylidene diphenol

A number of suggested processes describe merely leaching crude bisphenol with a solvent or mixture of solvents selected to dissolve maximum amounts of by-products and minimum amounts of bisphenol. However, the bisphenol obtained from such solvent leaching normally is not pure enough for polycarbonate production. The bisphenol can also be purified by a combination of vacuum distillation and solvent leaching techniques (U.S. Pat. Nos. 3,219,549 and 3,290,391). More complicated, but more effective methods involve crystallization from an organic solvent at a temperature and pressure above the atmospheric boiling point of the solvent (U.S. Pat. No. 3,673,262). In yet another process for purification of bisphenols, a mixture of the reaction product, water and a water immiscible organic solvent is heated to a temperature below the boiling point of the organic solvent to provide two liquid phases which are then cooled to crystallize the bisphenol (U.S. Pat. No. 3,535,389). U.S. Pat. No. 3,326,986 employs a similar process in which the crude bisphenol is heated and melted in water without any organic solvent. The melt is agitated, then cooled and the crystals washed with a chlorinated organic solvent, e.g., methylene chloride, to remove the impurities.

Recovery of the purified product by the crystallization procedure varies from about 50 percent to a rarely achieved 90 percent which adds considerably to the cost of the bisphenol product finally obtained. It is well known that the final product purity is inversely related to the yield. Higher product purity will give lower yield. Most literature on bisphenol purification through crystallization emphasizes the final product purity and neglects the product yield. Known processes provide a yield of from 50–95% of the desired p,p'-bis product. The most effective method to increase the yield is to convert the by-products in the residue back to useful bisphenol through acid-catalyzed rearrangement or isomerization in a phenol medium. In order to make such isomerization feasible, the by-product concentration in such residual streams has to be very high. It is an object of this invention to provide a bisphenol purification process with a high yield and a high purity final product. The ultimate object of this invention is to provide an efficient process for the production of high purity 2,2'-bis(4-hydroxyphenyl)propane and achieve a yield high enough to generate the residual stream having a by-product concentration sufficient to make the rearrangement reaction practical.

It has now been discovered that a pure 2,2'-bis(4-hydroxyphenyl)propane, having less than about 0.25% and even as low as 0.02% of the o,p'-isomer, can be prepared by (1) crystallizing the crude bisphenol A in the presence of water and an organic solvent, e.g., toluene, (2) mixing the remaining mother liquor (after stripping off water and toluene) with phenol and thereafter contacting with a cation exchange resin in acid form or hydrochloric acid to rearrange the by-products to the desired product, (3) stripping the phenol and recycling to the crystallizer of step 1 or to the primary bisphenol reactor. If a second crystallization is included following step 1, the lowest level of by-product in the final product can be achieved.

SUMMARY OF THE INVENTION

The present invention can produce an exceptionally pure bisphenol A, suitable for making polycarbonate resins, from crude bisphenol A having o,p'-bisphenol A content ranging from 0.2 to 20%. The product yield of p,p'-bisphenol A is consistently above 95%. In the present purification process, the crude bisphenol A having had any unreacted phenol and acetone as well as the water produced in the condensation reaction removed therefrom, is fed to a crystallizer and toluene and a critical amount of water added. The critical amount of water in the crystallizer feed is 2–9% by weight based on the amount of crude bisphenol. This mixture is heated to about 80°–100° C. where a single phase is formed, then slowly cooled to ambient temperature. During the cooling process, it is preferable to hold the temperature between 60°–80° C., the range at which crystals begin to form, for at least 1–30 minutes. The crystal slurry is thereafter further cooled slowly to ambient (20°–35° C.) temperature to complete the crystallization. The remaining mother liquor from this crystallization is distilled to remove water and toluene; phenol is added to the remainder. This mixture contains large amounts of o,p'-bisphenol A and other by-products and is passed through a bed of cation exchange resin (acid form) to convert most of the by-products to the desired p,p'-bisphenol A. The effluent from the cation exchange bed can be recycled to the bisphenol reactor or, after stripping the phenol, can be returned as feed to the crystallizer.

DETAILED DESCRIPTION OF THE INVENTION

In the process of the present invention, the ultimate purity and product yield are dependent on (1) the amount of impurity in the crude bisphenol, (2) the amount of solvent employed with respect to the crude bisphenol, (3) the amount of water in the feed mixture, (4) the temperature and hold time at the beginning of crystal formation, (5) the cooling rate, (6) the solvent selection, and (7) the number of stages of crystallization.

In the present invention using a single batch crystallizer and the optimized conditions, it has been discovered that greater than about 95% of the total impurities can be removed from the crude bisphenol feed, having o,p'-bisphenol content between 0.25 and 15%. It is a well known fact that the more solvent used in crystallization, the purer the crystallized product will be. However, the product recovery yield will suffer because more of the desired p,p'-bisphenol will remain in the mother liquor. It also requires more energy to strip off the solvent from the mother liquor when more solvent is used.

The amount of water in the crystallizer feed is very critical with respect to the final product purity. The presence of water in the feed mixture creates a bis-solvent-water (BSW) phase. It was discovered that the highest purity product and the highest yield of bisphenol could be obtained by crystallizing from this BSW phase. Although the bisphenol crystallizes from either solvent alone, e.g. toluene, or from a bis-water phase as suggested by the art, neither method is as effective as crystallizing from the BSW phase with respect to product purity and yield. In the present invention, a feed with single BSW phase is preferred because it can be handled more easily and more consistently in the process. The relative amount of water, solvent, crude bisphenol and temperature all contribute to the final phase status of the crystallizer feed mixture. There is an optimum water content needed, which depends upon the purity of the starting bis A, to achieve the highest purity in the final product. This water content is that which is necessary to obtain a single phase mixture. From one to four phases can exist in the feed mixture, depending on its composition and temperature.

The initial temperature of between 85° to 100° C. and atmospheric pressure is preferred to create a single BSW phase. It is necessary to increase temperature and operate above atmospheric pressure in order to achieve a single BSW phase if a smaller amount of solvent in the feed mixture is desired. The crystallizer temperature is lowered to a temperature within the range of about 60°–80° C. depending on feed composition, at which point crystallization begins. This is followed by cooling to room temperature (20°–30° C.) to obtain the remaining crystals. To avoid an undesirable high degree of supersaturation, cooling slowly to 60°–80° C. and holding there for a period of time sufficient to begin crystal formation is critical. This controls smooth growth of pure crystal nuclei, which is essential for final product purity. Alternatively, a small amount of purified bisphenol solid can be fed into the BSW phase while at a temperature of 60°–80° C., functioning as crystal nuclei to improve final product purity. Suitable solvents other than toluene and chloroform (principal solvents used as examples in this invention) that can be applied in the present invention are water immiscible solvents such as benzene, xylene, ethylene dichloride, 1,1,1-trichloroethane and methylene chloride. The optimized composition and conditions for solvents other than toluene will differ, but the principle is the same. The final product purity and yield also varies from solvent to solvent. In one method of purifying crude bisphenol A, phenol and acetone are removed from the reactor effluent and the crude bisphenol is fed to a crystallizer with water. The purified bisphenol A crystals are separated from the liquid phase, which is itself separated into a bis-water (BW) and aqueous phase. The BW phase containing high levels of by-product impurities is then treated according to the method of the present invention to produce additional purified bisphenol A by mixing with toluene in another crystallizer. Alternatively the crude bisphenol A from the reactor, having had the phenol and acetone removed is mixed with toluene and water in a crystallizer.

The following description of the process of the present invention is given with reference to the drawing. The crude bisphenol (free from excess phenol, acetone and water) or the BW phase from a previous water crystallization is fed from line 27 into the crystallizer 10, where water and toluene are also introduced through lines 28 and 29, respectively. The crystals of the purified bisphenol (p,p'-isomer) from the crystallizer 10 are fed to a wash vessel 11, where they are rinsed with toluene. The liquid phase containing the impurities (mainly the o,p'-isomer) from the crystallizer, along with the wash liquid from vessel 11 is fed via line 22 to a flash column 12 which removes the toluene and water overhead. The bottoms of the flash column 12 are then mixed with phenol from line 25 and passed via line 23 into an ion exchange bed 13 to convert the o,p'-isomer to the p,p'-bisphenol. The effluent from bed 13 is sent via line 24 to distillation column 14 wherein phenol is removed and recycled via line 25 to the feed to the ion exchange bed. The bottoms of column 14, now richer in p,p'-bisphenol are recycled via line 26 and mixed with the feed in line 27 to the crystallizer.

COMPARATIVE EXAMPLE A (Water Crystallization-Water Wash)

A typical run begins with 200 grams of crude bisphenol (2.6% o,p'-bis and 94–95% p,p'-bis) and 400 grams of water charged into a 1-liter flask. The mixture is heated with agitation until the bisphenol melts and a BW phase is reached. The agitated mixture is cooled slowly to the desired temperature and crystals are allowed to form for 1–2 hours. The crystals are then recovered by filtration and washed with hot water (95° C.). The percent product recovery and o,p'-bisphenol of the purified crystals are presented in Table I. The impurity rich oil coats the outer surface of the relatively purer bisphenol crystals and hot water wash removal is inefficient due to low solubility and selectivity of those impurities in water.

The data from this comparative example indicate that in a solely water purification system the o,p'-bisphenol in the final product can be reduced from 2.6% to 1% with product recovery above 75%. Higher purity can be achieved by additional hot water washing but much lower yields result. Water/bis ratio in Table I is by weight.

TABLE I

| Water Crystallization and Water Wash | | | |
|---|---|---|---|
| Water/Bis | Temp. °C. | % Recovery | % o,p'-Bis |
| 0/1* | 95 | 80 | 2.56 |
| 0.6/1 | 95 | 75.8 | 1.69 |
| 2.5/1 | 90 | 83.9 | 1.00 |
| 2/1 | 87.5 | 90.8 | 1.80 |
| 2.5/1 | 85 | 93.9 | 1.93 |

*Fed dry molten bis directly into water.

COMPARATIVE EXAMPLE B (Water Crystallization-Solvent Wash)

The feed for this example was crystals from Example 1. The crystals were washed at room temperature with solvent (chloroform or toluene) for 15-30 minutes with agitation. The solvent was then filtered off and the crystals were dried in an oven. The data for the solvent washing, or leaching, are presented in Table II. The solvent leaching improves significantly the final product purity but the o,p'-bisphenol contents are still too high for polycarbonate grade bis even after six consecutive leachings.

TABLE II

Water Crystallization and Solvent Leaching

| Initial % o,p'-Bis | Solvent/Bis | Number of Washes | Final % o,p'-Bis |
|---|---|---|---|
| 1.80 | 1/1, chloroform | 2 | 0.49 |
|  | 1/1, chloroform | 4 | 0.40 |
|  | 1/1, chloroform | 6 | 0.39 |
| 1.80 | 1/1, Toluene | 2 | 0.50 |
|  | 1/1, Toluene | 4 | 0.46 |
|  | 1/1, Toluene | 6 | 0.47 |

EXAMPLE 3

Data from Example 1 and 2 indicate that the combination of water crystallization and organic solvent leaching can improve the efficiency of bisphenol purification. A wet bisphenol melt (BW phase) was obtained, as in Example 1, by heating crude bisphenol and water (1:1 by weight) with agitation at 98°–100° C. Ceasing agitation allowed phase separation between the BW phase and water to occur. The BW layer (>95° C.) was slowly added into an agitated flask containing toluene at the desired temperature. After complete addition (~10 minutes), the mixture was allowed to cool until the initial precipitation of bisphenol crystals began (65°–68° C.). The mixture was maintained at that temperature for one hour. Afterwards, the mixture was cooled to a desired lower temperature and, once attained, allowed to agitate there for an additional one hour. The crystals were separated from the mother liquor by filtration and then washed with one weight (equivalent to the weight of original crude bisphenol) of toluene and dried in a vacuum oven. The results from this example and other similar experiments are presented in Table III. The final product purity was relatively lower if the mixture is not held at the temperature (65°–68° C.) when the crystallization begins. The final temperature of crystallization does not have much affect on the purity of the crystals, but the lower the temperature, the higher the yield. The p,p'/o,p' ratio in the mother liquor is lower when the final crystallization temperature is lower.

TABLE III

Addition of BW Phase Into Solvent and Crystallization from Solvent

| Solvent: Bis Ratio | Temp. °C. | % o,p'- Bisphenol | p,p'/o,p' in Mother Liquor | % Recovery |
|---|---|---|---|---|
| 2:1, Toluene:Bis | 60 | 0.38 | 2.99 | 91.3 |
| 2:1, Toluene:Bis | 80 |  |  |  |
|  | 68 |  |  |  |
|  | 40 | 0.17 | 1.48 | 88.5 |
| 1:1, Toluene:Bis | 80 |  |  |  |
|  | 66 |  |  |  |
|  | 25 | 0.19 | 0.469 | 92.1 |
| 1:1, Chloroform | 60 |  |  |  |
|  | 25 | 0.25 | 0.815 | 83.4 |

The crude bisphenol starting material contained 2.6% o,p'-bisphenol impurity.

EXAMPLE 4

This experiment was carried out similar to Example 3 except the quantity of water and time were reduced. The results are presented in Table IV. The final product purity remains about the same as in Example 3, yet the p,p'/o,p' ratio in the mother liquor is much lower. At this lower ratio the impurities rearrangement reaction is more efficient. As shown in Table IV, addition of the BW phase to toluene at the temperature of precipitation (65°–68° C.) results in almost the same final product purity and eliminates the need for a separate cooling step from 80° C. to 67° C. This example also shows that the quantity of water in the feed, the holding time and the temperature can each be reduced without affecting the final purity and yield of product. An equally pure product is obtained when toluene is recycled from the rinse to the crystallizer. Toluene/bis ratio was 1/1 for each run in Table IV.

TABLE IV

Reduction of Water Content and Crystallization Time

| H₂O/Bis Ratio | Temp. °C. | Time, Min. | % o,p'- Bisphenol | p,p'/o,p' in Mother Liquor | % Recovery |
|---|---|---|---|---|---|
| 1:1 | 80 |  |  |  |  |
|  | 68 | 30 |  |  |  |
|  | 25 | 60 | 0.17 | 0.37 | 92.2 |
| 0.25:1 | 68 | 15 |  |  |  |
|  | 25 | 15 | 0.18 | 0.31 | 93.5 |
| 0.20:1 | 67.5 | 10 |  |  |  |
|  | 25 | 10 | 0.20 | 0.35 | 93.3 |

EXAMPLE 5

Example 4 suggested that the process of the invention could be further simplified by pre-mixing crude bisphenol, water and solvent before crystallization. This example illustrates how the feed composition affects the mixture phase state and its effect on final product quality. Crude bisphenol, water and solvent of a desired ratio were charged into a flask with an agitator and heat supply. The temperature of the mixture was brought up to its boiling point and then slowly cooled to 25° C. The resulting crystals are filtered and washed with solvent. When water is not introduced into the crystallization feed, a higher temperature is required to dissolve the crude bisphenol and its product purity is not as high as that crystallized from the BSW phase with optimized water content. With proper feed composition, a single phase of BSW was formed and the crystals produced from it were excellent. The formation of a single phase mixture as feed for the crystallizer in this crystallization process will simplify the plant operation but is not a necessity. Seeding the single phase (BSW) mixture with a small quantity of pure Bis A results in a product of almost equal quality and comparable yield.

TABLE V

Crystallization from Pre-Mixed Bis-Toluene-Water

| B:T:W | Temp. (°C.) Where BTW Phase Forms | Boiling Point of Mixture | p,p'/o,p' in Mother Liquor | % o,p'- Bisphenol in Product | Kind and Number of Phases |
|---|---|---|---|---|---|
| 1:2:0 | 110 | 110.8 | 0.86 | 0.24 | 1L (T) |
| 2:4:1 | 78–80 | 85 | 0.56 | 0.34 | 3L (W+T+BTW) |
| 4:8:1 | 78–80 | 85 | 0.63 | 0.20 | 3L (W+T+BTW) |
| 4:8:1 | 78–80 | 85 | 0.58 | 0.15 | 1L (BTW) |
| 16:32: 0.92 | 78–80 | 85 | 0.40 | 0.14 | 2L, 1S (T+BTW+B) |

Note:
B - Bisphenol (solid), 2.6% o,p'-bisphenol
T - Toluene (liquid)
W - Water (liquid)
L - Liquid phase
S - Solid phase
BTW - Bisphenol-toluene-water phase

EXAMPLE 6

The quantity of water in the crystallization feed affecting the number and kinds of phases and the final product quality was previously demonstrated in Example 5. In this example it was determined that optimum quantity of water was needed to achieve the best final product while maintaining a constant bisphenol/toluene ratio. The crude bisphenol from this example has much higher impurity concentrations than either Example 4 or 5 (4.8–5.2%, o,p'-isomer). A mixture of 30 parts bisphenol, 70 parts toluene and the desired amount of water is heated to 87° C. and held there about ten minutes. The resulting mixture, present in several possible phase states, depending on the amount of water in the feed is then allowed to cool slowly to about 35° C. after removal of the heat source. The final crystals are filtered, rinsed with toluene, and then oven-dried. The results from this example are presented in Table VI. The data clearly shows the optimum water content necessary to produce the purest final crystal product. The purest final product is obtained from the feed having one liquid phase or which contains a small quantity of crystals. This prevents oversaturation during the cooling process. The final product purity is further improved when the crystallizer temperature is held constant at 78° C. for a few minutes before further cooling. As the presence of water is reduced to below one part per 100 parts toluene/bisphenol mixture, the amount of solid phase in the mixture is increased but the purity is lower. Crystal seeds with relatively lower purity always result in less pure final crystals. When the quantity of water in the feed mixture is increased to three parts or more, two or three liquid phases are formed. The final product becomes less pure as the water content is increased and multiple liquid phases are formed. This example illustrates the advantage of optimizing water content and the importance of pure crystal seeds.

TABLE VI

Optimization of Water Content*
The feed mixture contained 70 parts toluene and 30 parts bisphenol.

| Water, Parts | Final Product % o,p'-Bisphenol | Feed Mix Before Cooling Phase State |
|---|---|---|
| 0 | 0.33 | 1L (T), 1S (B) |
| 1.0 | 0.27 | 1L (T), 1S (B) |
| 1.5 | 0.25 | 1L (T), 1S (B) |
| 2.0 | 0.21 | 1L (BTW), 1S (B) |
| 2.3 | 0.25 | 1L (BTW) |
| 2.3*, hold 5 min. at 78° C. | 0.21 | 1L (BTW) |
| 2.5 | 0.26 | 1L (BTW) |
| 3.0 | 0.34 | 2L (T+BTW) |
| 4.5 | 0.48 | 3L (T+W+BTW) |

*The crude bis feed contained 4.8-5.2% o,p'-bisphenol.

EXAMPLE 7

The impurity content of crude bisphenol will vary depending on the source. It can be fairly low when obtained from the preceeding crystallizer product in a 2-stage process or very high when obtained from the residue of a water crystallizer. In this example, the feed mixture composition is 70:30:2 toluene:bisphenol:water. This mixture is heated to about 92° C. where a single liquid phase is formed. The crystallizer is slowly cooled to 77° C. and held for five minutes at that temperature. The crystallizer is finally allowed to cool to 35° C. with continued agitation. The product crystals are filtered and immediately rinsed with fresh toluene before drying in an oven. Using fixed feed composition, the final product purity directly relates to the crude bisphenol purity. About 95% or higher o,p'-bisphenol content has been removed by a single crystallization for feed crude bisphenol having o,p'-bisphenol between 1.2 to 14%. Table VII illustrates that the purity of the final product will vary depending on the original crude bisphenol quality and number of stages of crystallizers.

TABLE VII

Effect of Impurity Contents

| Feed % o,p'- Bisphenol | Product % o,p'-Bisphenol | Phase State Before Cooling | % o,p' Reduction |
|---|---|---|---|
| 1.21 | 0.030 | 1L | 97.5 |
| 2.50 | 0.063 | 1L | 97.5 |

TABLE VII-continued

Effect of Impurity Contents

| Feed % o,p'-Bisphenol | Product % o,p'-Bisphenol | Phase State Before Cooling | % o,p' Reduction |
|---|---|---|---|
| 3.75 | 0.110 | 1L | 97.1 |
| 5.00 | 0.205 | 1L | 95.9 |
| 7.50 | 0.216 | 1L | 97.1 |
| 9.50 | 0.255 | 1L | 97.3 |
| 11.80 | 0.395 | 1L | 96.7 |
| 14.0 | 0.522 | 1L | 96.3 |

Thus, the above experiments indicate that the operable bis:solvent:water ratio is from about 1:0.5:0.01 to about 1:1:0.02 and preferably from about 1:1:0.02 to about 1:2:0.2.

We claim:

1. In a purification process for 4,4'-isopropylidene diphenol wherein the crude reaction product, or the mother liquor from a first crystallization thereof, is purified by dissolving in an organic liquid solvent and crystallized therefrom the improvement which comprises (1) mixing water and organic solvent together with said crude reaction product, in a crystallizer, wherein water is present in an amount of from 2 to 9% by weight based on said crude bisphenol, (2) heating said mixture to a temperature of about 80° to 100° C. sufficient to produce a single liquid phase, (3) reducing the temperature of said liquid phase to a lower temperature of about 60° to 80° C. and holding at that temperature for a time sufficient to begin crystallization, (4) reducing the temperature of said liquid phase further to an ambient temperature of about 20° to 35° C. to obtain the maximum yield of crystals of the said 4,4' product therefrom, (5) removing said solvent and water from the mother liquor from step 4, (6) mixing phenol with said mother liquor, (7) contacting the mixture of phenol and mother liquor at ambient temperature with a cation exchange resin in the acid form for a sufficient time to convert at least some of the impurities to the desired product, (8) removing phenol from said mixture, and (9) recycling the remainder to the crystallizer of step 1, and wherein the organic solvent in step 1 is benzene, toluene, xylene, methylene chloride, chloroform, ethylene dichloride or 1,1,1-trichloroethane and the entire process is accomplished under substantially atmospheric pressure.

2. The process of claim 1 wherein the bis:solvent ratio is from about 1:0.5 to about 1:2.

3. The process of claim 1 wherein a bisphenol-water phase is added to the solvent in the crystallizer in step 1.

4. The process of claim 1 wherein the crude reaction product contains from about 0.4 to about 14% by weight of the o,p'-bisphenol.

5. The process of claim 1 wherein crystals of 4,4'-isopropylidene diphenol are added in step 3 to begin the crystallization.

* * * * *